United States Patent [19]

Nardo

[11] 4,427,294

[45] Jan. 24, 1984

[54] APPARATUS FOR DENSITOMETRIC MEASUREMENT OF PROTEIC FRACTIONS SEPARATED BY ELECTROPHORESIS

[76] Inventor: Pietro Nardo, Via Galvani, 5, 20095 Cusano Milanino (MI), Italy

[21] Appl. No.: 311,774

[22] Filed: Oct. 15, 1981

[30] Foreign Application Priority Data

Oct. 21, 1980 [IT] Italy ............................. 25474 A/80

[51] Int. Cl.³ ........................................... G01N 21/22
[52] U.S. Cl. ................................. 356/344; 204/180 S; 204/299 R; 356/244; 356/444; 422/64
[58] Field of Search ................. 356/344, 444, 73, 244; 204/180 S, 299 R; 422/64

[56] References Cited

U.S. PATENT DOCUMENTS

| | | | |
|---|---|---|---|
| 3,669,554 | 6/1972 | Horer et al. | 356/244 |
| 4,090,791 | 5/1978 | Siddiai et al. | 356/244 X |
| 4,117,338 | 9/1978 | Adrion et al. | 356/73 X |

FOREIGN PATENT DOCUMENTS

| | | | |
|---|---|---|---|
| 2838646 | 3/1979 | Fed. Rep. of Germany | 356/344 |
| 3090 | of 1906 | United Kingdom | 350/532 |

OTHER PUBLICATIONS

Spiegel et al., "Messdatenerfassung bei der Elektrophorese", *Elektronik,* vol. 26, No. 5, pp. 67–71, 5/77.

*Primary Examiner*—William L. Sikes
*Assistant Examiner*—Matthew W. Koren
*Attorney, Agent, or Firm*—Cushman, Darby and Cushman

[57] ABSTRACT

An indexing fixture with many seats can be rotated in such a way as to present in each succeeding time interval a different seat at a reader. An electronic processing unit can control, under the control of a keyboard, different sequences of presentation of said seats of the indexing fixture and different modes of presentation of the detected data on an optical display, a graphic recorder and a magnetic recorder.

5 Claims, 5 Drawing Figures

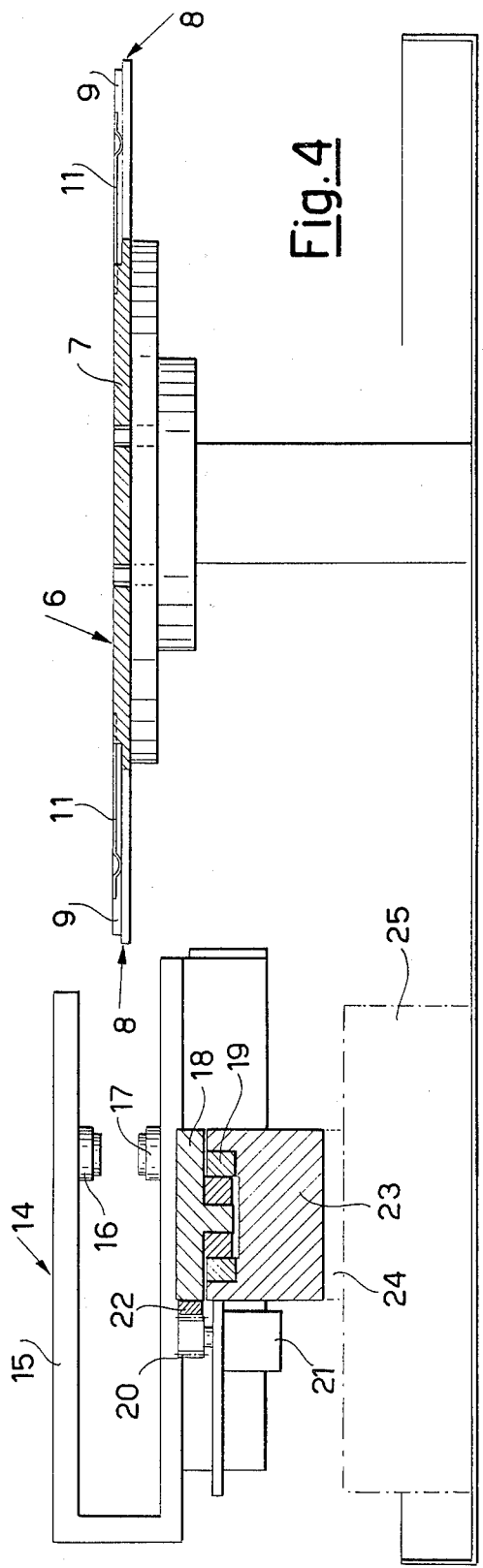
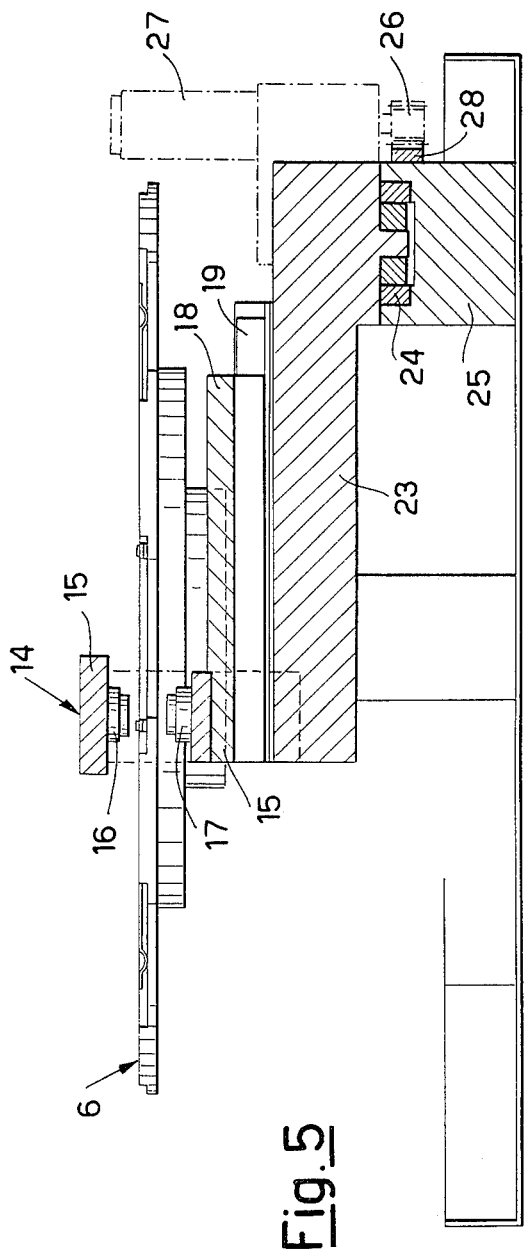

APPARATUS FOR DENSITOMETRIC MEASUREMENT OF PROTEIC FRACTIONS SEPARATED BY ELECTROPHORESIS

The present invention relates to an apparatus for densitometric measurement of proteic fractions separated by electrophoresis.

It is known that electrophoresis is a system often used in medical analysis to separate various substances of different features contained in a liquid sample, particularly different proteic fractions of a bloodsample. Such a system consists of applying to the sample placed on a destined support-plate, a given potential difference which causes a different migration of the various component fractions according to their electric charge, their weight, their size and so on. The sample is then immersed in a dye, which shows the quantitative distribution of the various fractions and finally allows the measurement, by means of a densitometer, as a function of their colouring intensity.

It is already known that some densitometers, after having inserted in a suitable space a transparent plate with a blood-sample previously submitted to electrophoresis, read the various parallel layouts in which the sample is distributed. A microcomputer processes the reading results and displays them visually on a graphic display, as well as, in certain cases, on an electrooptic one.

A common disadvantage of the known densitometers is that they have a rather low measurement rate, essentially deriving from the fact that no more than one or at most two samples at a time may be inserted in the space destined to analysis. It therefore is necessary to proceed to the substitution of a new sample or samples with consequent stopping of the apparatus.

Besides, always for the same reason, the apparatus can only be operated in one way, repeating always the same operations and not allowing operator cycle variations according to different needs for the system.

In view of this, the object of the present invention is to realize an extremely flexible apparatus, which guarantees a high rate of measurement and at the same time a very wide range of working cycles according to operator wishes.

SHORT STATEMENT OF THE INVENTION

According to the invention this object is reached by an apparatus characterized in that it comprises a rotating indexing fixture with many seats, in each of which a support with a sample to be analyzed may be loaded. A reader is arranged in such a way as to be met in succession by said seats. A driving means causes the combined radial and tangential movement of said reader with respect to said indexing fixture. An optical display, a graphic recorder, a magnetic recorder, a control keyboard and a processing electronic unit control different sequences of presenting the indexing fixture seats at said reader and different ways of presenting the data detected on said optical display, on said raphic recorder and on said magnetic recorder according to the orders given by said keyboard.

The use of a rotating indexing fixture with many seats clearly allows the apparatus to analyze without stop a multiplicity of samples, with a consequent increase of the work rate. On the other hand, through the keyboard and the processing unit, it is possible to vary the reading sequence of the different samples without being obliged to remain bound to the spatial succession of the different indexing fixture seats and by choosing, on the contrary, the most suitable sequence for the present moment. Always through the keyboard and the processing unit it is moreover possible to choose among a number of possibilities of processing and presentation of the detected data, by making the apparatus to work automatically from the beginning to the end or, for example, by showing on the optical display intermediate data to be checked visually and recording at the end on the graphic and/or magnetic recorder only the final results of the analysis.

Substantially, the apparatus according to the invention appears as a very useful analysis instrument, which makes possible high work rates, as well as differentiated operations which adapt it each time to the different needs of the operator.

BRIEF DESCRIPTION OF THE DRAWINGS

An exemplary embodiment of the apparatus according to the invention is illustrated for better clarity in the enclosed drawings, in which:

FIG. 4 shows the assembly of FIG. 2 in section along line IV—IV of FIG. 3; and

FIG. 5 shows said assembly in section along line V—V of FIG. 3.

DETAILED DESCRIPTION OF THE PREFERRED EMBODIMENT

Figure 1:
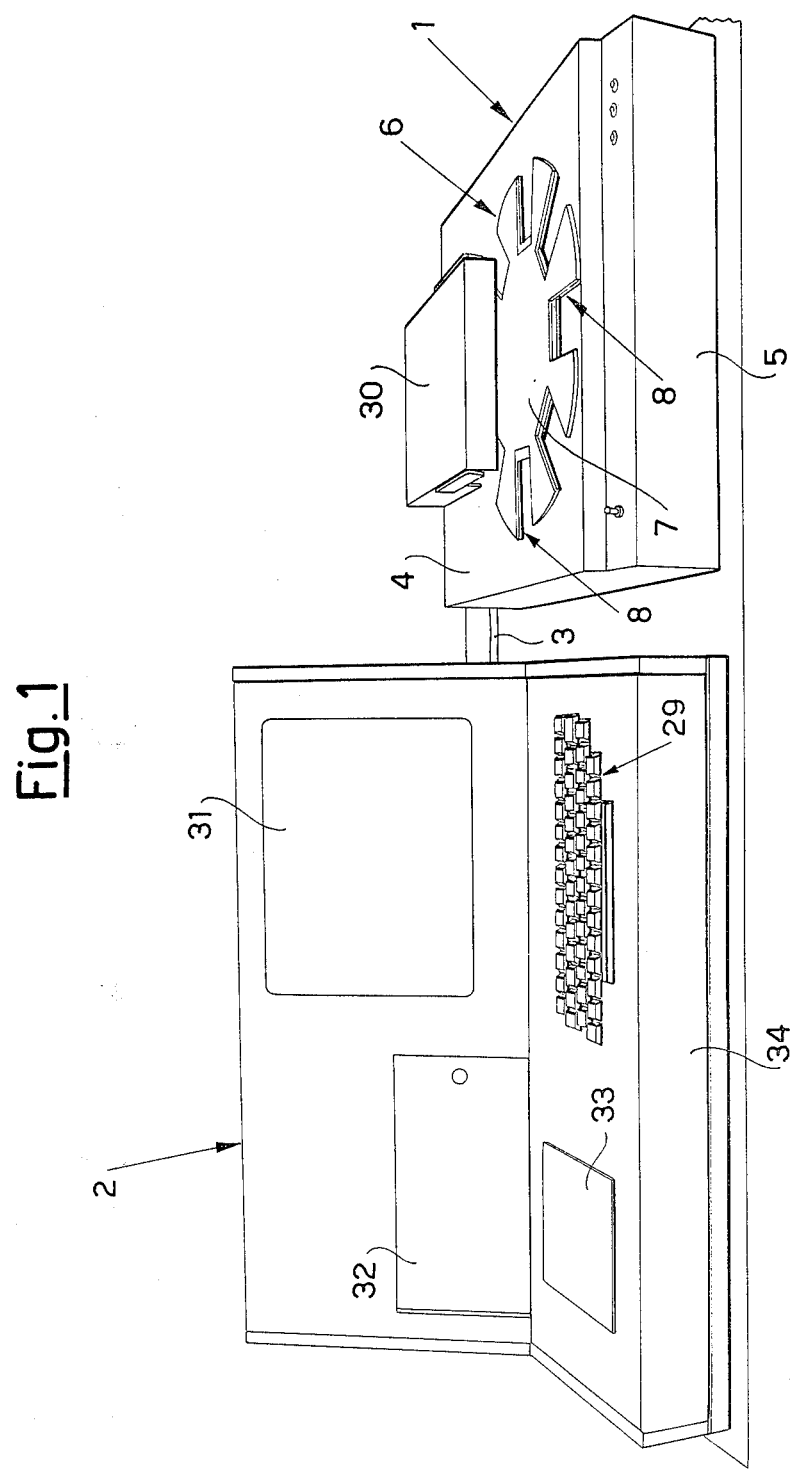
FIG. 1 shows in a schematic, perspective view the assembly of an apparatus according to the present invention.

As shown in FIG. 1, the apparatus illustrated in the drawings is comprised of a reading unit 1 and a control, processing, visualizing and recording unit 2. The two units are connected to one another by an electric cable 3.

Figure 2:
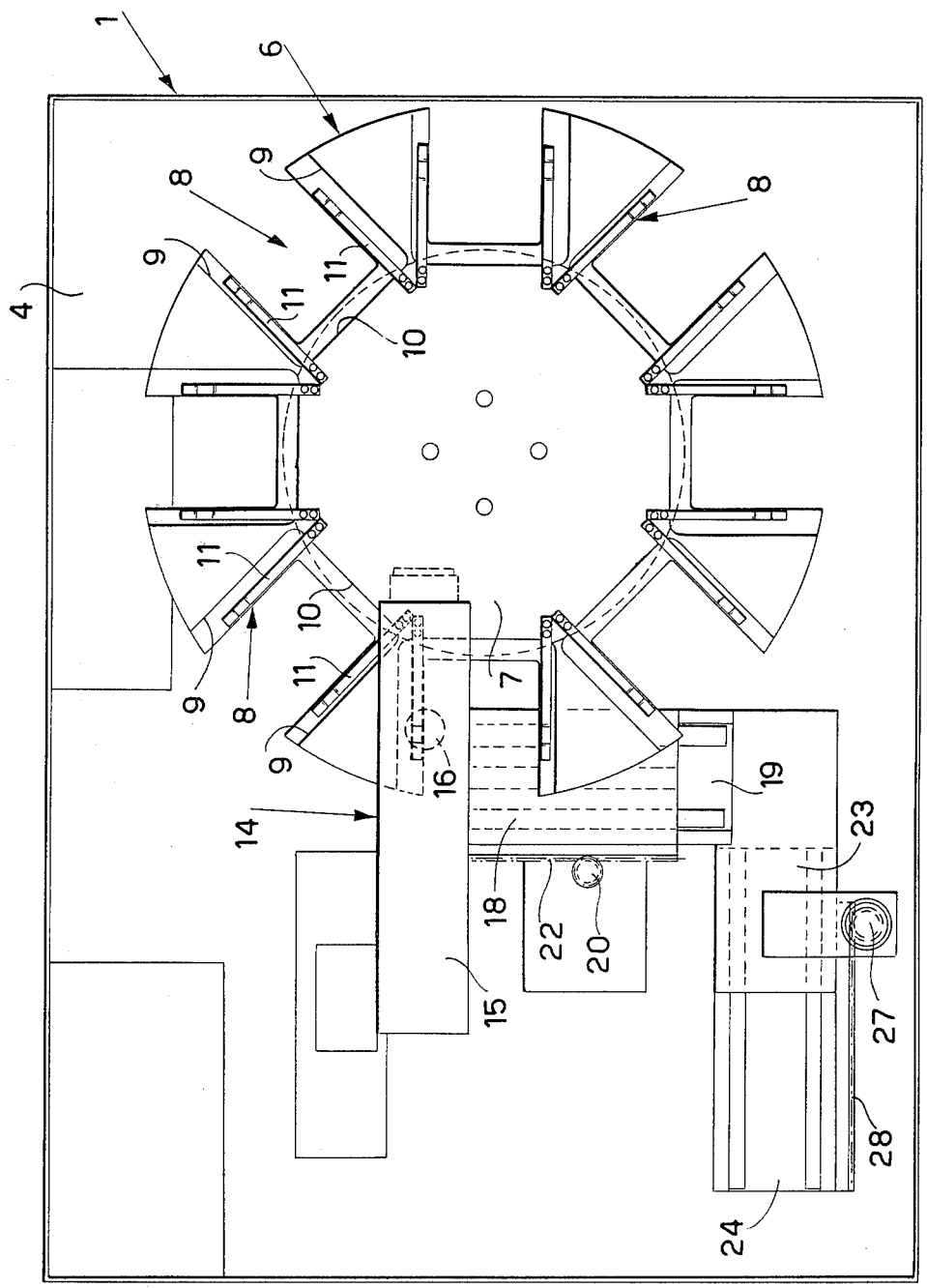
FIG. 2 shows in top plan view, the part of said apparatus, which comprises the indexing fixture, the reader and the relative driving mechanism.
Figure 3:
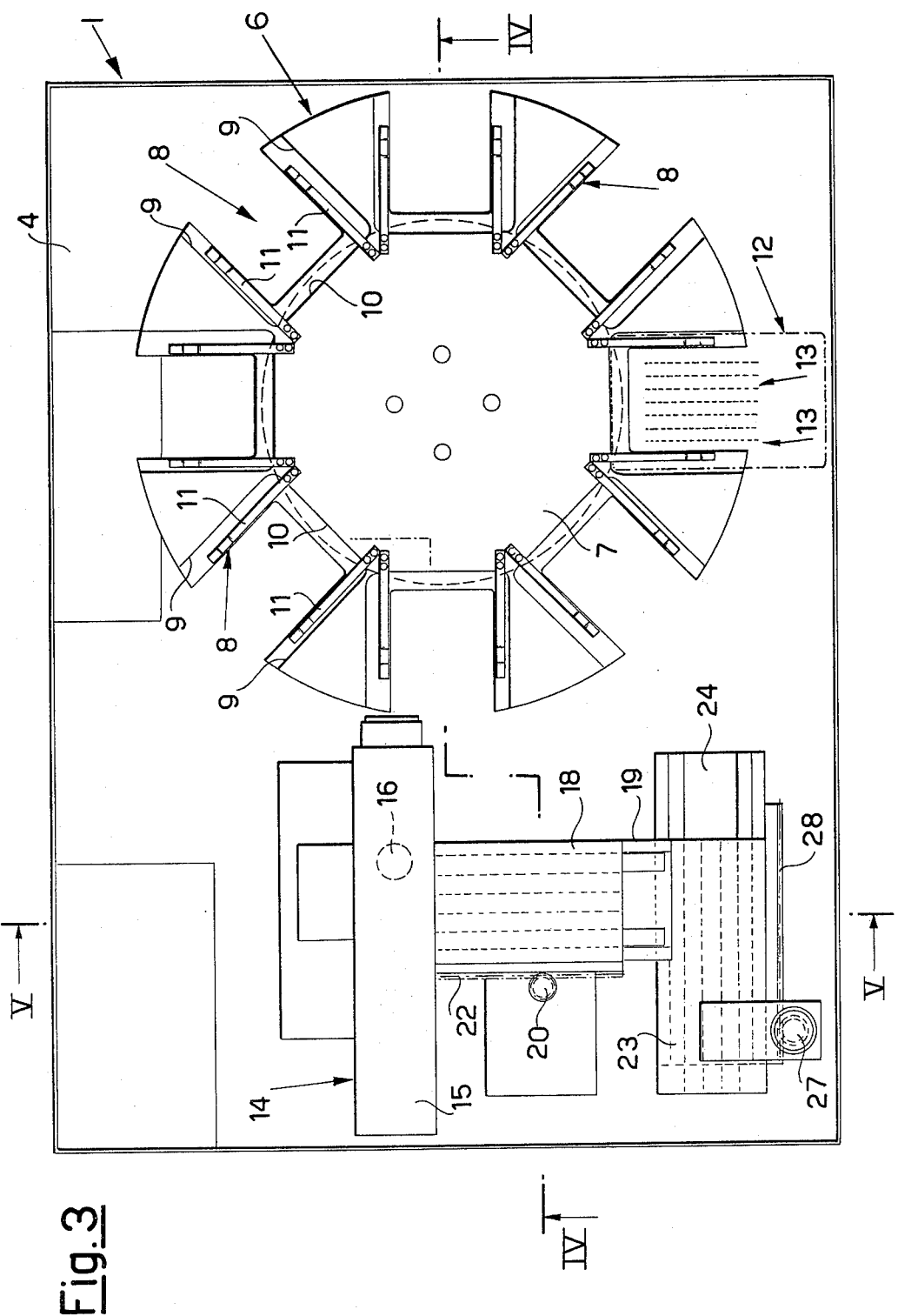
FIG. 3 shows in top plan view the same part of the apparatus of FIG. 2, with the reader in a different position with respect to the indexing fixture.

Above the upper closure plane 4 of a casing 5, the reading unit 1 includes a rotating indexing fixture 6 comprising a circular plate 7 provided with a plurality of equally circumferentially spaced radial seats 8. As shown in FIGS. 2–4, every seat 8 is delimited laterally by two undercuts 9 and frontally by a further undercut 10 and moreover is provided with a pair of lateral flat springs 11, all of which retain in the seat (under the same springs), a plate with the sample to be analyzed, which is inserted in each time in said seat. By way of example, in FIG. 3 there is shown a plate 12 with electrophoretic layouts 13, which is situated in a suitable position in a seat of the indexing fixture 6.

Through the rotation of the indexing fixture 6 (under the control of conventional drive means not illustrated in the drawings) every seat 8 can be brought to a photoelectric-cell reader 14, which is disposed at an indexing fixture side under a turnable cover 30 (FIG. 1) and comprises (FIG. 4) a U-like support and two opposite photoelectric-cells 16 and 17, the one being a transmitter and the other a receiver or vice-versa.

The U-like support 15 is rigidly restrained to a first slide 18 capable of tangential movement (with respect to the indexing fixture 6) along a first guide 19 under the control of a sprocket 20 operated by a motor 21 and engaged with a rack 22 integral with the slide 18. The guide 19 in its turn is a part of a second slide 23, which is movable in radial direction (always with respect to the indexing fixture 6) along a second guide 24 integral with a fixed support 25, under the control of a sprocket 26 operated by a motor 27 and engaged with a rack 28 integral with the support 25. The above mentioned possibilities of movement of the slides 18 and 24, to which there correspond similar capabilities of movement of the reader 14 with respect to the indexing fixture 6, are clearly shown in FIGS. 2-5.

The adjacent unit 2 comprises a keyboard 29, through which the operator can give the apparatus the desired orders, appropriately processed by a microprocessor situated in the inside of a case 34 and therefore not illustrated in FIG. 1. The unit 2 also comprises an optical display, the screen 31 of which is represented in FIG. 1, a graphic recorder accessible through a door 32 and a magnetic-cassette recorder situated in a seat obtained below a door 33.

For the purpose of employing the apparatus illustrated in the drawings for densitometric measurement of the substances that form fluid-samples of various kinds, usually blood-samples, the operator charges the indexing fixture 6 with as many transparent plates like that indicated with 12 in FIG. 3 as there are radial seats 8 of the indexing fixture.

By making the indexing fixture 6 suitably rotate, the first sample to be analyzed is brought to the reader 14, which is at the beginning in the rest position of FIG. 2. Under the control of the motor 27 and through the engagement existing between the sprocket 26 and the rack 28, the reader 14 is then moved back together with the slide 23 to the position of FIG. 3, which is fixed by a suitable micro-switch and constitutes the starting position of the reading cycle of the selected sample.

The initial movement of the reader 14 is caused by the simultaneous operation of the two sprockets 20 and 26, which through the slides 18 and 23 cause a diagonal displacement of the reader until it is aligned with the first layout 13 of the plate. Thereupon, sprocket 26 causes the rectilinear advancement of the reader along the above mentioned layout for the detection of the colour intensity of the different spots which compose it, through the photoelectric-cell system 16 and 17.

At the end of the exploration of the first layout, another micro-switch controls the reverse of the sprocket movement 26 for the return of the reader to a back return position with a completely rectilinear movement.

Through the simultaneous operation of the sprockets 20 and 26, the reader then moves to the second layout, which it explores with the same previous modalities, and as it will do later for the other layouts of the same plate.

While the reader 14 carries out in the aforesaid way, the reading of the different layouts of the plates under examination, the results of the reading are successively presented on the optical display 31 and eventually introduced, automatically or not, at once or at the end of reading of the whole plate, into the graphic and/or the magnetic recorder, according to the program set out by the operator.

The same or a different procedure is then repeated for another plate, which, once more according to the program set out, can be that located in a seat immediately following the first one along the circumference of the indexing fixture 4 or one located at another seat at will.

Substantially it is the operator who, in a kind of direct "conversation" with the apparatus, preliminary sets out and follows the working thereof, making the choice which most corresponds to his needs.

There is also to be noted the importance of the separation of the apparatus into two different units (1 and 2) connected through an electric cable. In fact, this allows, if desired, substitution of the reading unit with another one having the same features but complete with self-loading devices and/or other accessories, without the necessity of changing or modifying the control, processing, visualizing and recording unit, which is surely the most complicated and expensive part.

I claim:

1. Apparatus for densitometric measurement of proteic fractions separated by electrophoresis comprising: a rotating indexing fixture with a plurality of circumferentially spaced seats, in each of which a support with a sample to be analyzed may be loaded, a reader arranged in such a way as to be met in succession by said seats, driving means for causing a combined radial and tangential movement of said reader with respect to said indexing fixture, an optical display, a graphic recorder, a magnetic recorder, a control keyboard and an electronic processor means for controlling different sequences of presenting the indexing fixture seats at said reader and different modes of presenting the detected data on said optical display, on said graphic recorder and on said magnetic recorder according to the orders given through said keyboard.

2. Apparatus according to claim 1, wherein said indexing fixture includes a rotating plate provided with a plurality of equally circumferentially spaced radial seats.

3. Apparatus according to claim 2, wherein each of said seats is delimited by a frontal undercut and by two lateral undercuts and is provided with flat springs for retaining the support of the sample to be analyzed.

4. Apparatus according to claim 1, wherein said reader comprises a U-like support with overlapped horizontal arms bearing respective photoelectric-cell elements facing one another, said support being ridgidly connected to a first slide slidingly connected to a second slide slidingly connected to a support base, said first slide being capable of rectilinear movement in tangential direction with respect to said indexing fixture and said second slide being capable of rectilinear movement in radial direction with respect to said indexing fixture.

5. Apparatus according to claim 1, wherein said indexing fixture and said reader are included in a reading unit and said keyboard, said electronic processor, said optical display and said recorders are included in a control, processing, visualizing and recording unit, said units being mechanically separated from one another and functionally connected through an electric cable.

* * * * *